(12) United States Patent
Albright et al.

(10) Patent No.: US 9,283,176 B2
(45) Date of Patent: Mar. 15, 2016

(54) BENZIMIDAZOLE ANTHELMINTIC COMPOSITIONS

(75) Inventors: Robert Bruce Albright, Chalfont, PA (US); Moses Collumbus Lawrence, Dayton, NJ (US); Shobhan Shashikant Sabnis, Pennington, NJ (US); Sivaja Ranjan, Princeton Junction, NJ (US)

(73) Assignee: Zoetis Services LLC, Florham Park, NJ (US)

( * ) Notice: Subject to any disclaimer, the term of this patent is extended or adjusted under 35 U.S.C. 154(b) by 968 days.

(21) Appl. No.: 12/573,289

(22) Filed: Oct. 5, 2009

(65) Prior Publication Data

US 2010/0087497 A1 Apr. 8, 2010

Related U.S. Application Data

(60) Provisional application No. 61/103,675, filed on Oct. 8, 2008.

(51) Int. Cl.
| | |
|---|---|
| *A01N 43/52* | (2006.01) |
| *A61K 31/4184* | (2006.01) |
| *A01N 43/02* | (2006.01) |
| *A01N 43/04* | (2006.01) |
| *A01N 43/08* | (2006.01) |
| *A01N 43/12* | (2006.01) |
| *A01N 43/14* | (2006.01) |
| *A01N 43/16* | (2006.01) |
| *A01N 43/22* | (2006.01) |
| *A61K 31/365* | (2006.01) |
| *A61K 9/00* | (2006.01) |

(52) U.S. Cl.
CPC .............. *A61K 9/0017* (2013.01); *A01N 43/02* (2013.01); *A01N 43/04* (2013.01); *A01N 43/08* (2013.01); *A01N 43/12* (2013.01); *A01N 43/14* (2013.01); *A01N 43/16* (2013.01); *A01N 43/22* (2013.01); *A01N 43/52* (2013.01); *A61K 31/365* (2013.01); *A61K 31/4184* (2013.01)

(58) Field of Classification Search
CPC ....... A01N 43/02; A01N 43/04; A01N 43/08; A01N 43/12; A01N 43/14; A01N 43/16; A01N 43/22; A01N 43/52; A61K 31/365; A61K 31/4184
See application file for complete search history.

(56) References Cited

U.S. PATENT DOCUMENTS

| | | | |
|---|---|---|---|
| 4,197,307 A | 4/1980 | Gallay et al. | |
| 4,436,737 A | 3/1984 | Boray | |
| 5,468,765 A | 11/1995 | Banks et al. | |
| 5,824,653 A | 10/1998 | Beuvry et al. | |
| 5,840,324 A | 11/1998 | Hennessy et al. | |
| 6,165,987 A | 12/2000 | Harvey | |
| 6,267,985 B1 | 7/2001 | Chen et al. | |
| 6,340,672 B1 | 1/2002 | Mihalik | |
| 6,489,303 B2 | 12/2002 | Jancys | |
| 2005/0226908 A1* | 10/2005 | Huron et al. | 424/442 |
| 2005/0245468 A1 | 11/2005 | Rowe et al. | |
| 2006/0121072 A1 | 6/2006 | Shepherd | |
| 2006/0293260 A1* | 12/2006 | Albright | 514/28 |
| 2007/0060509 A1* | 3/2007 | Kanikanti et al. | 514/9 |
| 2007/0128239 A1 | 6/2007 | Hayes et al. | |
| 2008/0003282 A1* | 1/2008 | Soll et al. | 424/464 |
| 2009/0036458 A1* | 2/2009 | Fattohi et al. | 514/250 |

FOREIGN PATENT DOCUMENTS

| | | |
|---|---|---|
| EP | 0045655 | 2/1982 |
| EP | 0059074 | 9/1982 |
| EP | 0146414 | 6/1985 |
| EP | 0427582 A | 5/1991 |
| EP | 0717993 A2 | 6/1996 |
| FR | 2755824 A1 | 5/1998 |
| GB | 2252730 A | 8/1992 |
| WO | 95/23590 A | 9/1995 |
| WO | 99/43206 A | 9/1999 |
| WO | 00/61068 | 10/2000 |
| WO | 00/74489 A1 | 12/2000 |
| WO | 0105232 | 1/2001 |
| WO | 03/092680 A1 | 11/2003 |
| WO | 2004/043445 A1 | 5/2004 |
| WO | 2008/098168 A | 8/2008 |

OTHER PUBLICATIONS

CN02153428, Nov. 11, 2002, Machine Translation of Claims.

* cited by examiner

*Primary Examiner* — Kara R McMillian

(74) *Attorney, Agent, or Firm* — Paul M. Misiak

(57) ABSTRACT

The present invention provides a veterinary anthelmintic composition that includes: at least 10% w/v of a benzimidazole anthlemintic; and b) a water-immiscible solvent system, which comprises a lactone solvent, an essential oil, and surfactant.

12 Claims, 4 Drawing Sheets

BENZIMIDAZOLE ANTHELMINTIC COMPOSITIONS

CROSS-REFERENCE TO RELATED APPLICATIONS

This application claims the benefit of U.S. Provisional Application No. 61/103,675, filed Oct. 8, 2008, the contents of which are incorporated herein by reference in their entirety.

BACKGROUND OF THE INVENTION

Helminthiasis is a widely occurring disease affecting animals, particularly warm-blooded animals, causing substantial economic losses. Particularly susceptible to the infections are sheep, cattle, goats, horses, and other domesticated herbivores. Many know anthelmintic agents have been discovered possessing varying degrees of efficacy on the particular helminths causing the infections. Certain classes of anthelmintics have a greater or lesser spectrum of activity, i.e., they are able to treat infections involving a wider or smaller range of parasites.

A particularly useful class of anthelmintics are those of the avermectin and milbemycin classes, exemplified by abamectin, ivermectin, doramectin, milbemycin D and moxidectin. These have activity against parasitic roundworms and also against some ectoparasites, but lack activity against cestodes and trematodes (flukes).

Liver fluke is a global disease which mainly infects cattle and sheep but can also develop in many other animals including horses, pigs, goats, rabbits and at least in Australia, native animals such as kangaroos and wombats. Humans may also be infected with liver fluke. Liver fluke can cause serious economic losses. Global losses due to liver fluke disease are estimated at over three billion U.S. dollars per year. In sheep, infection with liver fluke reduces production including wool growth and wool quality, lambing percentages and growth rates of lamb. Sheep can also die as a result of liver fluke infection.

Benzimidazoles, including triclabendazole, are well known for their anthelmintic activity. Triclabendazole is a particularly useful anthelmintic, having activity primarily vis a vis trematodes, and particularly against liver flukes. Triclabendazole is described in U.S. Pat. No. 4,197,307, and is also known as 5-chloro-6(2,3-dichlorophenoxy)-2-methylthio-1H-benzimidazole. Triclabendazole is highly effective against liver flukes at all stages of their life cycle, including early immature fluke, immature fluke and adult liver fluke.

A combination of anthelmintic actives, which would have the spectrum of activity of the avermectin/milbemycins and triclabendazole is desirable. However, successful combination formulations must provide for physical stability of the formulation for a commercially reasonable period of time; chemical stability of the actives therein; maintain or exceed the level of pharmacological activity of the individual actives, and be administrable to the animal in a suitable dosage form.

It is advantageous to have liquid formulations which contain the anthelmintic active(s) and which are easily administered to the animal by being poured on the backs of animals. Liquid formulations of therapeutic agents may be in the form of a solution or a suspension. Due to the highly insoluble nature of triclabendazole, it has been difficult to provide liquid formulations containing triclabendazole. As a result, anthelmintic formulations containing triclabendazole have usually been prepared as suspensions. However, suspension formulations have several disadvantages. By its very nature, the particulate matter in a suspension may settle or sediment to the bottom of the container upon standing. Such sedimentation may also lead to caking and solidification of the sediment with a resulting difficulty in redispersing the suspension upon agitation. The sedimentation causes further problems as it results in differences in the concentration of the active agent in the formulation. This is turn leads to difficulties in determining and obtaining the effective and safe dose for treatment of the animals. Suspensions are also less able to be absorbed when applied by way of pour-on administration.

For these reasons, it would be desirable to provide pour-on liquid formulations, which contain triclabendazole in the form of a solution, rather than in the form of a suspension. Solutions are sometimes required to obtain sufficient bioavailability. Solutions are liquid preparations that contain one or more chemical substances dissolved in a suitable solvent or mixture of mutually miscible solvents. However, substances in solutions are often more susceptible to chemical instability than those in the solid state.

When formulating anthelmintic compositions, it is necessary that the compositions maintain both the chemical activity of the active compounds, as well as the physical stability of the formulation. This allows for the compositions to be prepared well in advance of their intended use, and to also have a useful shelf life as a commercial product.

Furthermore, a suitable pour-on liquid formulation would preferably include solvents having the ability to effectively penetrate the skin, thereby making the anthelmintic active(s) more likely to be systemically absorbed by the animal. Preferably, a suitable pour-on formulation would have a low freezing point and low surface tension to help with administration as a pour-on, and would be highly water repellant to inhibit wash off from the animal during rain or other water exposure.

SUMMARY OF THE INVENTION

The present invention provides a veterinary anthelmintic composition that includes at least 10% w/v [preferably 10-40% w/v, e.g., 15-25% w/v] of a benzimidazole anthelmintic in a water-immiscible solvent system, which comprises a lactone solvent, an essential oil, and surfactant.

Furthermore, this invention provides a veterinary anthelmintic composition, including 10-40% w/v, and preferably about 15% to about 25% w/v of triclabendazole in a water immiscible solvent system, which comprises γ-hexalactone, 1,8-cineole, and polyethylene glycol caprylic/capric glycerides.

Also provided is a method of treating parasites in a homeothermic animal. The method includes administering to the homeothermic animal a veterinary anthelmintic composition including at least 10% w/v [preferably 10-40% w/v, e.g., 15-25% w/v] of a benzimidazole anthelmintic in a water-immiscible solvent system, which comprises a lactone solvent, an essential oil, and surfactant.

The invention further provides a method of treating parasites in a homeothermic animal. The method includes administering to the animal a veterinary anthelmintic composition comprising at least 10% w/v [preferably 10-40% w/v, e.g., 15-25% w/v] of triclabendazole in a water immiscible solvent system, which comprises γ-hexalactone, 1,8-cineole, and polyethylene glycol caprylic/capric glycerides.

Furthermore, the invention provides a process of preparing a veterinary composition. The process includes combining a benzimidazole anthelmintic with a water-immiscible solvent system, which comprises a lactone solvent, an essential oil, and surfactant.

DETAILED DESCRIPTION OF THE INVENTION

Figure 1:
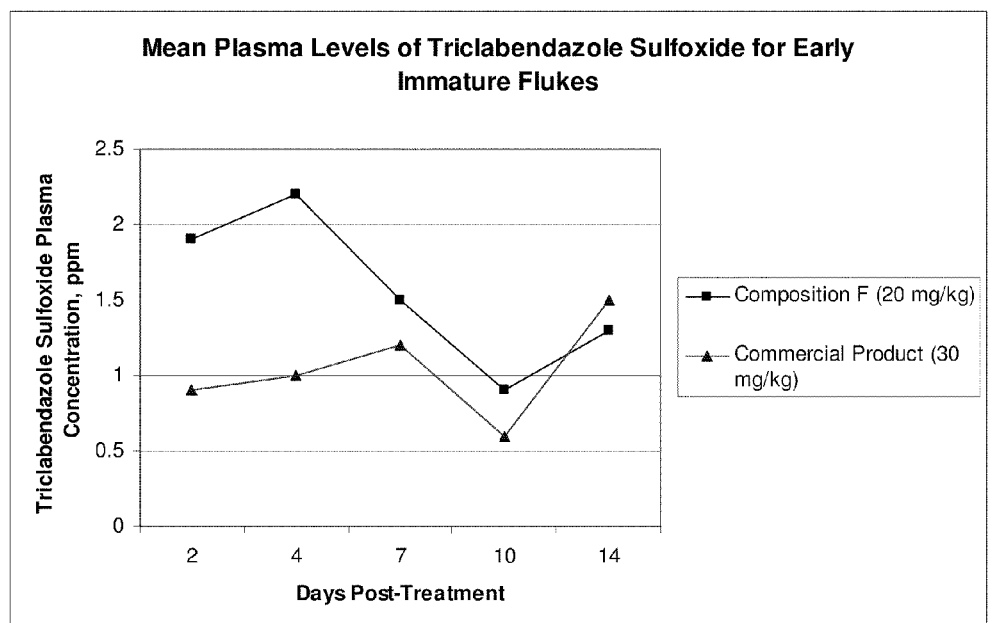
FIGS. 1 through 4 are graphs of the amount of triclabendazole sulfoxide (the pharmacologically active metabolite of triclabendazole) present in the plasma of cattle treated with compositions from Examples 3 and 4 over the 14 days post treatment.

The invention relates to veterinary compositions including a benzimidazole anthelmintic. Benzimidazoles are used to treat endoparasitic diseases in domestic animals and are characterized by a broad spectrum of activity and low toxicity. In one embodiment, the composition includes a benzimidazole in combination with another anthelmintic compound, such as a macrocyclic lactone.

The veterinary anthelmintic composition comprises at least 10% w/v of a benzimidazole anthelmintic in a water-immiscible solvent system, which comprises a lactone solvent, an essential oil, and a surfactant. In one embodiment, the composition is a pour-on composition.

In one embodiment, the veterinary anthelmintic composition includes about 15% to about 25% w/v of triclabendazole in a water immiscible solvent system, which comprises γ-Hexalactone, 1,8-cineole, and polyethylene glycol caprylic/capric glycerides.

As used herein, the term "water-immiscible solvent system" is intended to mean a nonaqueous system of three or more solvents, which solvents when combined, are substantially incapable of mixing or attaining homogeneity with water. In general, the water-immiscible solvent system has a low level of solubility in water, e.g. the solubility of the solvent mixture in water is less than 10% w/w, especially less than 5% w/w.

The term "pour-on composition" and the like as used herein is intended to mean a composition wherein a particularly preferred route of administration is pour-on administration. Typically, "pour-on" formulations are referred to as such because they are poured-on the animal's back, usually from the withers to the tailhead of animals, such as cattle, sheep or horses.

As used herein, "benzimidazole" designates a veterinary compound of the benzimidazole chemical family such as thiabendazole, cambendazole, parbendazole, mebendazole, fenbendazole, oxfendazole, oxibendazole, albendazole, albendazole sulfoxide, thiophanate, febantel, netobimin, triclabendazole, salts thereof, or combinations thereof.

The term "macrocyclic lactone" as used herein designates a pharmaceutical compound in the avermectin or milbemycin family of compounds including avermectins such as ivermectin, abamectin or doramectin and milbemycins such as milbemycin D or moxidectin, or combinations thereof.

As used herein, the term "w/w" designates weight/weight, the term "w/v" designates weight/volume, and the term "mg/kg" designates milligrams per kilogram of body weight.

As described above, the compositions may include a benzimidazole compound in combination with another anthelmintic compound, such as a macrocyclic lactone. It is desirable to administer the benzimidazole compound in combination with a macrocyclic lactone to enhance the spectrum of parasites to be controlled. Ideally, veterinary compositions containing both a benzimidazole and a macrocyclic lactone would be stable, bioavailable and easy to administer as a pour-on.

Benzimidazoles, when used in combination with at least one additional anthelmintic, such as macrocyclic lactones or aminoacetonitriles, offer complimentary parasite control in homeothermic animals. For example, triclabendazole is active against liver flukes but only modestly active against round worms or ectoparasites, and moxidectin (a macrocyclic lactone) is highly active against round worms and ectoparasites, but with minimal activity as a flukicide. Moreover, depsipeptides, such as emodepside, and aminoacetonitriles, such as monepantel, are active against roundworms.

Surprisingly, it has now been found that a benzimidazole compound and a macrocyclic lactone may be formulated as a clear, homogeneous, water-immiscible solution suitable for pour-on administration to a homeothermic animal. Advantageously, the composition is self-emulsifying so that the benzimidazole active ingredient remains in solution and is bioavailable. The anthelmintic composition is effective against all stages of fluke and has excellent transdermal penetration. Moreover, the composition has low surface tension, good water-repellancy and a low freezing point, which are all desirable characteristics for a pour-on formulation.

Benzimidazoles suitable for use in the composition include thiabendazole, cambendazole, parbendazole, mebendazole, fenbendazole, oxfendazole, oxibendazole, albendazole, albendazole sulfoxide, thiophanate, febantel, netobimin, triclabendazole, and combinations thereof. In one preferred embodiment, the benzimidazole anthelmintic is triclabendazole. Triclabendazole is highly effective against liver fluke at all stages of their life cycle.

Lactone solvents suitable for use in anthelmintic compositions include, but are not limited to, the following: γ-hexalactone, butyrolactone, δ-hexalactone, γ-dodecalactone, δ-nonalactone, δ-decalactone, γ-decalactone, and δ-dodecalactone and other alkyl lactones and combinations thereof. Triclabendazole has surprisingly good solvency in these lactones, and similiar lactones and combinations. In a preferred embodiment, the lactone solvent is γ-hexalactone.

The oil component of the composition is preferably an essential oil selected from, but not limited to, the following: 1,8-cineole (also known as Eucalyptol), 1,4-cineole, Euganol, limonene oil, Tea Tree oil, citronellol and combinations thereof. In one embodiment, the essential oil component is 1,8-cineole.

Surfactants suitable for use in the composition include, but are not limited to, the following classes of emulsifiers or surfactants: polyethylene glycol fatty acid esters, polyethylene glycol glycerol fatty acid esters, alcohol-oil transesterification products, polyglycerized fatty acids, propylene glycol fatty acid esters, mono-, di- and triglycerides and combinations thereof. Nonionic surfactants may be preferable.

In one preferred embodiment, the surfactant is a mixture of mono-, di-, and triglycerides and mono- and di-fatty acid esters of polyethylene glycol. For example, a suitable surfactant is LABRASOL® (Gaftefosse, Saint-Priest, France), which is composed mainly of PEG esters and glycerides with medium acyl chains. LABRASOL® is also known as polyethylene glycol-8 (PEG-8) caprylic/capric glycerides. Another suitable surfactant is PEG-6 caprylic/capric glycerides. Other surfactants suitable for use in the compositions are those such as polyethylene glycol monolaurate, polyethylene glycol dilaurate, polyethylene glycol monooleate, polyethylene glycol dioleate or glycerin polyethylene glycol coconut oil.

As described above, the composition may optionally include at least one anthelmintic in addition to the benzimidazole compound. In one embodiment, at least one additional anthelmintic is selected from the following: macrocyclic lactones, tetramisole, levamisole, depsipeptides (e.g., emodepside), aminoacetonitriles (e.g., monepantel) and combinations thereof.

In one embodiment, the composition may include a macrocylic lactone or an aminoacetonitrile. Macrocyclic lactones suitable for use in the composition of the invention include milbemycin D, avermectin, ivermectin, abamectin, doramectin, moxidectin and combinations thereof. Aminoacetonitriles include monepantel. In one preferred embodiment, the composition includes moxidectin.

The effective amounts of the anthelmintic compounds, such as benzimidazole, macrocyclic lactone and/or aminoacetonitrile compounds, may vary according to the potency of the compounds, the method of application, the host animal, the target parasite, the degree of infestation, or the like. In one embodiment, a benzimidazole is present in an amount of about 10% to about 40% w/v. In general, amounts of about 15-25% w/v, of a benzimidazole such as triclabendazole are preferred, and amounts of about 0.01-2.0% w/v, preferably 0.5% w/v of a macrocyclic lactone, such as moxidectin, are suitable.

The composition includes a water-immiscible solvent system comprising a lactone solvent, an essential oil, and a surfactant. The lactone solvent may be present in the composition in an amount of about 10% to about 40% w/v. The essential oil may be present in an amount of about 5% to about 50% w/v. In a preferred embodiment, the essential oil is present in an amount of about 10% to about 35% w/v. The surfactant is present in an amount of about 30% to about 60% w/v. In a preferred embodiment, the surfactant is present in an amount of about 40% to about 50% w/v.

Advantageously, the veterinary composition provides easy administration and effective bioavailability of the anthelmintic ingredients. Accordingly, the present invention provides a method of treating parasites in a homeothermic animal, which comprises administering to said animal a composition comprising at least 10% w/v of a benzimidazole anthelmintic in a water-immiscible solvent system, which comprises a lactone solvent, an essential oil, and a surfactant.

In one embodiment, the treatment method includes administering to the animal a veterinary anthelmintic composition comprising about 15% to about 25% w/v of triclabendazole in a water immiscible solvent system, which comprises γ-hexalactone, 1,8-cineole, and polyethylene glycol caprylic/capric glycerides.

In one embodiment of the methods, the benzimidazole anthelmintic is triclabendazole. The triclabendazole may be present in the administered composition in an amount of about 10% to about 40% w/v.

In another embodiment of the methods, the administered composition further includes at least one additional anthelmintic selected from, but not limited to, the following: macrocyclic lactones, tetramisole, levamisole, depsipeptides, aminoacetonitriles and combinations thereof. In one preferred embodiment, the additional anthelmintic is moxidectin. The moxidectin is preferably present in an amount of about 0.01 to about 2% w/v.

In one embodiment of the methods, the composition includes γ-hexalactone as the lactone solvent. The lactone solvent may be present in an amount of about 10% to about 40% w/v.

In a further embodiment of the methods, the essential oil component is 1,8-cineole. The essential oil may be present in an amount of about 5% to about 50% w/v.

In yet another embodiment of the methods, the surfactant is a mixture of mono-, di-, and triglycerides and mono- and di-fatty acid esters of polyethylene glycol. The surfactant may be present in an amount of about 30% to about 60% w/v.

In one embodiment, the compositions may be administered to the animal as pour-on compositions. Typically, a pour-on composition is administered to the skin of the animal from withers to tail-head.

Homeothermic animals suitable for treatment in the method include: swine, cattle, sheep, horses, goats, camels, water buffalos, donkeys, fallow deer, reindeer, or the like, preferably swine, cattle, horses or sheep.

In actual practice, the composition of the invention may be administered in dose rates of mg of active anthelmintic ingredient per kg of body weight of the host animal. Dose rates suitable for use in the method of invention will vary depending upon the mode of administration, the species and health of the host animal, the target parasite, the degree of infection or infestation, the breeding habitat, the potency of the additional parasiticidal compound, and the like.

The present invention also provides a process of preparing a veterinary composition. The process includes combining i) a benzimidazole anthelmintic with ii) a water-immiscible solvent system comprising a lactone solvent, an essential oil, and surfactant. In one embodiment, said combining comprises dissolving the benzimidazole anthelmintic in a solution of the surfactant to form a benzimidazole/surfactant solution; and mixing the benzimidazole/surfactant solution with the essential oil and the lactone solvent to form the composition.

In one embodiment, the process further includes adding at least one additional anthelmintic to the composition. In one embodiment, the at least one additional anthelmintic is a macrocyclic lactone, an aminoacetonitrile or a combination thereof. In another embodiment of the process, a stabilizing agent may be added to the composition. In one embodiment, the stabilizing agent is butylated hydroxytoluene (BHT).

Macrocyclic lactones suitable for use in the process of preparation include milbemycin D, avermectin, ivermectin, abamectin, doramectin, moxidectin, or combinations thereof, preferably moxidectin.

Aminoacetonitriles suitable for use in the process of preparation include monepantel.

Benzimidazoles suitable for use in the process of preparation include thiabendazole, cambendazole, parbendazole, mebendazole, fenbendazole, oxfendazole, oxibendazole, albendazole, albendazole sulfoxide, thiophanate, febantel, netobimin, triclabendazole, or combinations thereof, preferably triclabendazole.

As will be clear to persons skilled in the art, where compositions according to the present invention are to be used, or are to be prepared for use, in veterinary medicine, they may also contain additional carriers, stabilizing agents, buffering agents, preservatives or other excipients well know in the art.

For a more clear understanding of the invention, the following examples are set forth hereinbelow. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLES

Example 1

Process of Preparing Anthelmintic Compositions

A pour-on veterinary anthelmintic composition may be prepared according to the following procedure. LABRA- SOL® (a surfactant) was added to a mixing tank and the surfactant was heated to about 60° C. Thereafter, triclabendazole was added to the heated surfactant. Heating was discontinued once a solution formed. The solution was then allowed to cool to about 40° C., after which time 1,8-Cineole (an essential oil) was added to the mixing tank with continued mixing. When the solution had cooled to about 30° C., γ-hexalactone was added with continued mixing. A stabilizer, such as butylated hydroxytoluene (BHT), was then added to the mixing vessel and mixed until dissolved. Thereafter, moxidectin was added and mixed until dissolved. The resulting solution was filtered through a 2 μm filter cartridge (Pall Corporation, East Hills, N.Y.) and packaged into bottles suitable for pour-on veterinary applications.

While the foregoing describes one preferred embodiment of the process, it is well within the contemplation of the present invention that the components may be added in a different order. For example, in another embodiment, the lactone solvent is added first to the mixing tank, followed by the addition of the essential oil with continued mixing. Thereafter, the benzamidazole anthelmintic is added, followed by the surfactant. Heat may be applied to facilitate the formation of a solution at one or more steps during the process. Subsequently, the solution is allowed to cool to about 25-30° C., and the stabilizer is then added and mixed until dissolved. Moxidectin, or another suitable anthelmintic agent, is then added and mixed until dissolved. The resulting composition is filtered and packaged similar to as described above.

Example 2

Pour-On Veterinary Compositions

Table I below illustrates various embodiments of anthelmintic compositions representative of the present invention. These compositions are suitable for administration as a pour-on in homeothermic animals, such as cattle, deer and/or sheep.

TABLE I

Embodiments of Anthelmintic Compositions

| Component | Composition A (% w/v) | Composition B (% w/v) | Composition C (% w/v) | Composition D (% w/v) |
|---|---|---|---|---|
| Triclabendazole | 25.0 | 25.0 | 20.0 | 20.0 |
| Moxidectin | 0.42 | 0.42 | 0.5 | 0.5 |
| BHT | 0.5 | 0.5 | 0.5 | 0.5 |
| γ-Hexalactone | q.s. ad | 34.0 | q.s. ad | 34.0 |
| 1,8-Cineole | 7.0 | q.s. ad | 7.0 | q.s. ad |
| PEG400 laurate | 45.0 | — | 45.0 | — |
| LABRASOL ® | — | 45.0 | — | 45.0 |

Example 3

Fluke Trial

A trial with cattle infected with liver flukes was conducted in order to compare the efficacy of additional embodiments of the present invention containing: i) moxidectin at 0.42% w/v or 0.5% w/v and ii) either 15, 20 or 25% triclabendazole, with two other treatments and a control. Table II below provides embodiments of the compositions employed for the present fluke trial.

TABLE II

Compositions for Fluke Trial of Example 3

| Component | Composition E (% w/v) | Composition F (% w/v) | Composition G (% w/v) |
|---|---|---|---|
| Triclabendazole | 15 | 20 | 25 |
| Moxidectin | 0.5 | 0.5 | 0.42 |
| BHT | 0.5 | 0.5 | 0.5 |
| γ-Hexalactone | 14.0 | 14.0 | 34.0 |
| 1,8-Cineole | 29.0 | 29.0 | q.s. ad |
| LABRASOL ® | q.s. ad | q.s. ad | 45.0 |

The animals were divided into twelve treatment groups of eight animals. Animals in Groups 1 to 3 received Composition E. Animals in Groups 4 to 6 received Composition F. Animals in Groups 7 and 8 received Composition G. Animals in Groups 9 and 10 received a commercial flukicide containing 0.5% w/v abamectin and 30% w/v triclabendazole. Animals in Group 11 received a commercial composition containing 0.5% w/v moxidectin to evaluate nematode efficacy only. Animals in Group 12 received no treatment. All animals were experimentally infected with *Fasciola hepatica* on Day 0. Treatments occurred on Days 28 (early immature), Day 42 (Immature) and Day 84 (Adult). Cattle were sacrificed between Days 96 and 100 of the study, when fluke counts were performed. Treatment compositions were administered as a pour-on to the back of the animal from the withers to the tailhead.

During the fluke trial, the amount of triclabendazole sulfoxide (an active metabolite of triclabendazole) present in the plasma was measured over the 14 days post-treatment using reversed-phase high-performance liquid chromatography analysis according to known methods. The presence of triclabendazole sulfoxide in the plasma of the animal indicated the parent drug was being absorbed through the skin of the animal and metabolized by the liver. In order to effectively treat liver fluke infection, triclabendazole anthelmintics need to reach their specific receptor inside the parasite cell to exert their action. Total worm counts were performed using procedures well known in the art.

The guidelines used for evaluating the efficacy of the anthelmintic compositions are described in the following references: World Association for the Advancement of Veterinary Parasitology (WAAVP) 2nd Edition of guidelines for evaluating the efficacy of anthelmintics in ruminants (bovine, ovine, caprine). I. B Wood et al., Veterinary Parasitology, 58 181-213 (1995); and Good Clinical Practices. VICH GL9. International Cooperation on Harmonization of Technical Requirements for Registration of Veterinary Medicinal Products.

Figure 2:
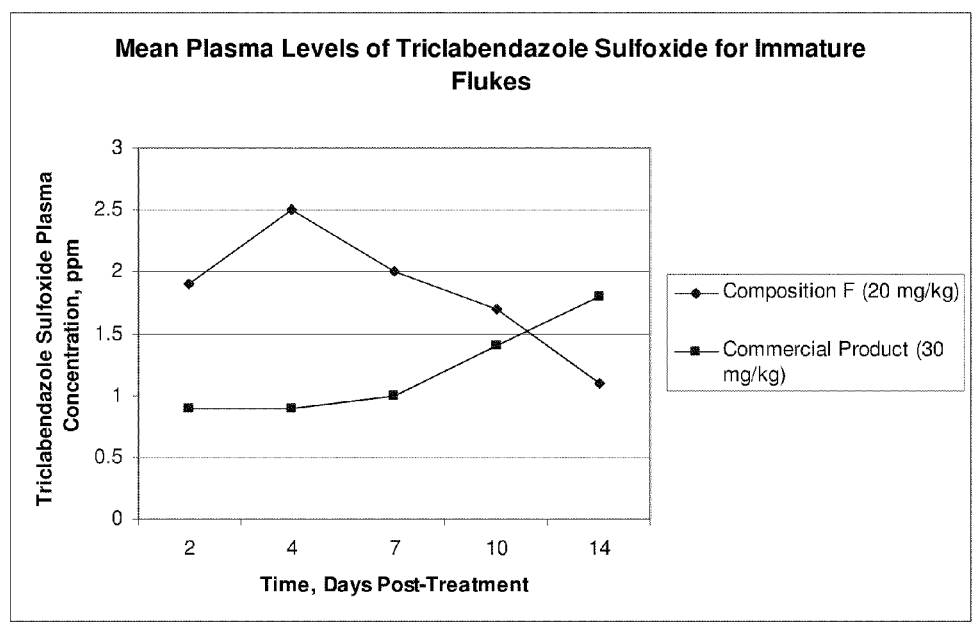

Triclabendazole sulfoxide was determined in the plasma of the treatment groups, which received Compositions E, F, or G, as well as those treatment groups which received the commercial flukicide. Surprisingly, higher levels of the sulfoxide metabolite were found in the plasma of animals treated with Composition F at a dose rate of 20 mg/kg triclabendazole, as compared to the commercial flukicide at a dose rate of 30 mg/kg triclabendazole. See FIGS. 1 and 2, which show the pharmokinetic profiles for triclabendazole sulfoxide where treatment occurred on Day 28 for early immature flukes (FIG. 1) or Day 42 for immature flukes (FIG. 2). While not bound by any one theory, it is highly likely that the solvent system used in the present compositions increases penetration into the animal's skin, making the active more likely to be absorbed and metabolized by the liver.

The fluke efficacy results of the trial are shown in Table III where Group efficacy is calculated relative to the animal group which received no treatment. In Table III, "moxi", "tricla" and "Tx" are abbreviations for "moxidectin", "triclabendazole" and "treatment", respectively. A day of treatment of 28 days corresponds to treatment for 4-week old early immature flukes. A day of treatment of 42 days corresponds to treatment for 6-week old immature flukes. Moreover, a day of treatment of 84 days corresponds to treatment for 12-week old adult flukes.

TABLE III

Animal Group Efficacies

| Group | Treatment Composition | Dose Rate | Day of Tx | Stage of Fluke | Efficacy (%) |
|---|---|---|---|---|---|
| 1 | E | Moxi 0.5 mg/kg + Tricla 15 mg/kg | 28 | Early Immature | 77.8 |
| 2 | E | Moxi 0.5 mg/kg + Tricla 15 mg/kg | 42 | Immature | 92.5 |
| 3 | E | Moxi 0.5 mg/kg + Tricla 15 mg/kg | 84 | Adult | 99.7 |
| 4 | F | Moxi 0.5 mg/kg + Tricla 20 mg/kg | 28 | Early Immature | 89.7 |
| 5 | F | Moxi 0.5 mg/kg + Tricla 20 mg/kg | 42 | Immature | 99.5 |
| 6 | F | Moxi 0.5 mg/kg + Tricla 20 mg/kg | 84 | Adult | 99.8 |
| 7 | G | Moxi 0.5 mg/kg + Tricla 30 mg/kg | 28 | Early Immature | 92.4 |
| 8 | G | Moxi 0.5 mg/kg + Tricla 30 mg/kg | 42 | Immature | 99.4 |
| 9 | Comparative (abamectin/tricla) | abamectin 0.5 mg/kg + Tricla 30 mg/kg | 28 | Early Immature | 88.1 |
| 10 | Comparative (abamectin/tricla) | abamectin 0.5 mg/kg + Tricla 30 mg/kg | 42 | Immature | 99.0 |

The results presented in Table III show that Compositions E, F and G were effective against early immature, immature and adult stages of fluke, with Compositions F and G showing the greatest efficacy.

Moreover, the results further indicate that Composition F administered at a dose rate of 20 mg/kg triclabendazole (Groups 4-6), was as effective against both early immature and immature flukes as a commercial flukicide administered at a dose rate of 30 mg/kg triclabendazole (Groups 9-10).

Example 4

Summary of Results Obtained from Other Cattle Trials

Table IVa below shows the compositions used in a comparative plasma level study in cattle.

TABLE IVa

| | % W/V | | | Comparative Commercial |
|---|---|---|---|---|
| Component | AA | BB | CC | Product |
| Triclabendazole | 20 | 20 | 20 | 30% w/v Triclabendazole Contains 0.5% w/v Abamectin |
| Moxidectin, | 0.5 | 0.5 | 0.5 | |
| BHT | 0.5 | 0.5 | 0.5 | |
| γ-Hexalactone | 34 | 14 | 14 | |
| Cineole | q.s. | 29 | 45 | |
| LABRASOL ® | 45 | q.s. | q.s. | |

Figure 3:
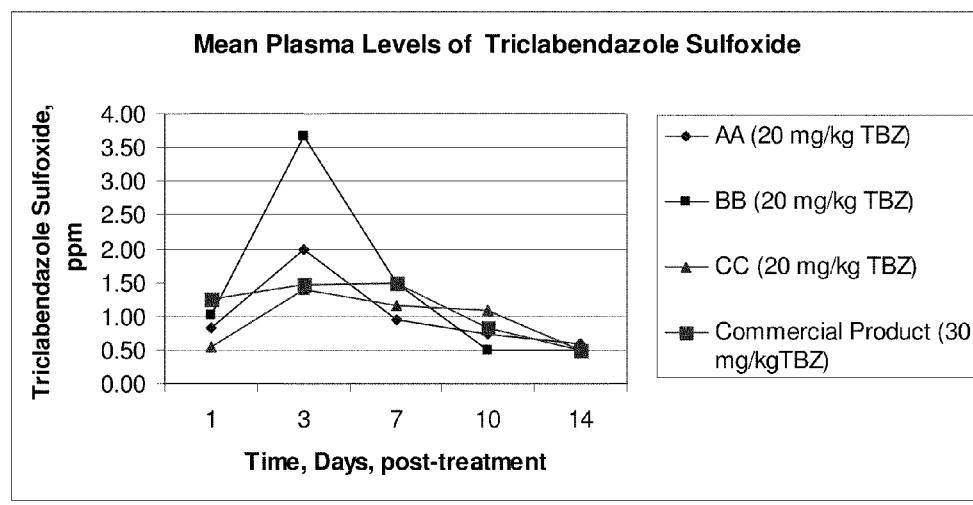

The accompanying FIG. 3 is a graph of the amount of triclabendazole sulfoxide present in the plasma of animals from the trial over 14 days post-treatment. As described earlier, the presence of triclabendazole sulfoxide in the plasma of animals indicates that the triclabendazole is being absorbed through the skin of the animal and metabolized by the liver. The accompanying FIG. 3 summarizes the differences seen among the different formulations outlined in Table IVa. Note the equivalent or greater plasma levels with formulations AA, BB and CC all dosed at 20 mg/kg triclabendazole (TBZ) compared to the commercial product dosed at 30 mg/kg triclabendazole. This indicates that the compositions in the present invention were better able to penetrate into the skin.

Another example of superior transdermal absorption of the invention is outlined in Table IVb below which shows the compositions used in another comparative fluke study.

TABLE IVb

| | % w/v | | | |
|---|---|---|---|---|
| Component | DD | EE | FF | GG |
| Triclabendazole | 25 | 25 | 20 | 20 |
| Moxidectin | 0.42 | 0.42 | 0.5 | 0.5 |
| BHT | 0.5 | 0.5 | 0.5 | 0.5 |
| γ-Hexalactone | q.s. | 34 | q.s. | 34 |
| Cineole | 7 | q.s. | 7 | q.s. |
| PEG400 laurate | 45 | — | 45 | — |
| LABRASOL ® | — | 45 | — | 45 |

Figure 4:
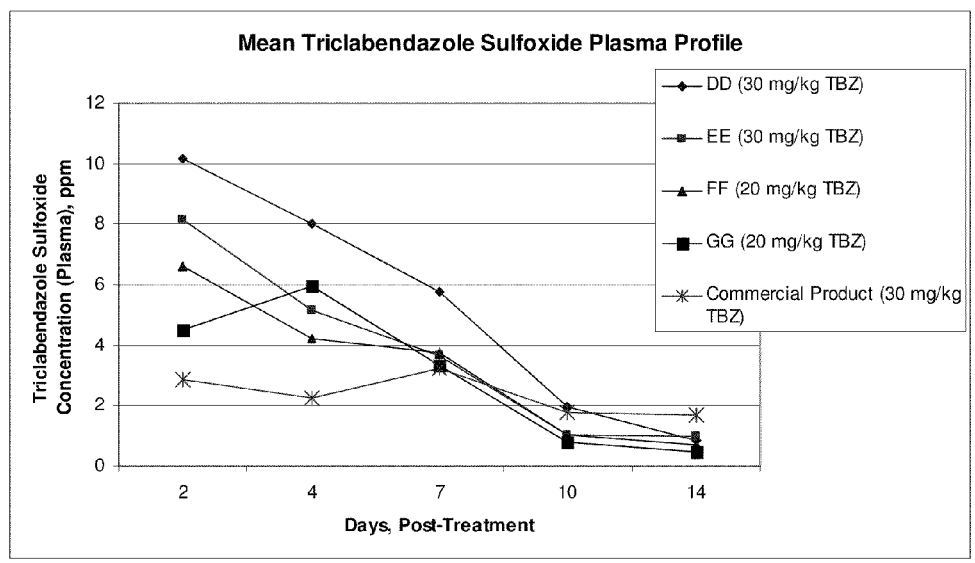

The accompanying FIG. 4 is a graph of the amount of triclabendazole sulfoxide present in the plasma of cattle from the fluke trial over 14 days post-treatment. As described earlier, the presence of triclabendazole sulfoxide in the plasma of animals indicates that the triclabendazole is being absorbed through the skin of the animal and metabolized by the liver. The accompanying FIG. 4 summarizes the differences seen among the different formulations outlined in Table IVb. Formulations DD and EE were dosed at 30 mg/kg, the recommended dose for the commercial product, whereas Formulations EE and FF were dosed at the rate of 20 mg/kg. Formulations FF and GG surpass the commercial product's plasma pharmacokinetic profile with only two-thirds the dose. This indicates that the compositions in the present invention were better able to penetrate through the skin.

Example 5

Stability Studies

Stability studies were conducted to ensure that a composition according to the present invention was stable. Composition F of Example 3 was prepared according to the process described in Example 1 and stored at either ambient (25° C.) or 40° C. for a total period of 6 months. At the conclusion of each storage period shown in Table V below, samples were tested for total moxidectin and triclabendazole levels.

TABLE V

Results of Stability Studies

| | % w/v Moxidectin | | % w/v Triclabendazole | |
|---|---|---|---|---|
| | 25° C. | 40° C. | 25° C. | 40° C. |
| Initial | 0.504 | — | 20.01 | — |
| 1 month | 0.498 | 0.498 | 19.86 | 19.97 |
| 3 months | 0.508 | 0.511 | 20.30 | 20.88 |
| 6 months | 0.494 | 0.486 | 19.92 | 19.89 |

The results presented in Table V clearly demonstrate that the triclabendazole remained in solution during storage.

Moreover, both triclabendazole and moxidectin remained stable and active over the entire 6 month storage period.

Example 6

Physical Characteristics

The physical characteristics of Composition F were measured and the results are shown in Table VI below.

TABLE VI

Physical Characteristics

| Physical Characteristic | Composition F |
|---|---|
| Freezing Point, ° C. | −20 |
| Viscosity, cP | 39.2 |
| Surface Tension, Dyne/cm | 36.3 |
| Flash point, ° F. | >150 |
| Water repellency, % wash-off | 1 |
| Contact angle | 0° |

The results in Table VI indicate that the physical characteristics of a composition according to the present invention provide ideal characteristics for use as a pour-on composition. In particular, Composition F has a low freezing point (−20° C.), which helps with pour-on administration. Moreover, the low surface tension of Composition F permits the composition to spread easily on the animal's body. Furthermore, Composition F is highly water repellant, making the amount capable of being washed off with rain or other water exposure low, which is also a desirable characteristic for a pour-on composition.

Example 7

Further Embodiments of Anthelmintic Compositions

Table VII below illustrates further embodiments of anthelmintic compositions representative of the present invention. These embodiments are prepared according to the process described in Example 1, except that the composition is either prepared without moxidectin (Composition I) or an anthelmintic agent other than moxidectin, e.g., abamectin, is added (Composition J).

TABLE VII

Further Embodiments of Anthelmintic Compositions

| Component | Composition I (% w/v) | Composition J (% w/v) |
|---|---|---|
| Triclabendazole | 20 | 20 |
| Abamectin | 0 | 0.5 |
| BHT | 0.5 | 0.5 |
| γ-Hexalactone | 14.0 | 14.0 |
| 1,8-Cineole | 29.0 | 29.0 |
| LABRASOL ® | q.s. ad | q.s. ad |

Example 8

Still Further Embodiments of Anthelmintic Compositions

Still further embodiments of anthelmintic compositions representative of the present invention are prepared according to the process described in Example 1 above, except that lactone solvents other than γ-hexalactone are employed. In particular, the compositions are prepared with one of the following lactone solvents: butyrolactone, δ-hexalactone, γ-dodecalactone, δ-nonalactone, δ-decalactone, γ-decalactone, and δ-dodecalactone. Suitable amounts of triclabendazole, moxidectin, the stabilizing agent (e.g., BHT), the essential oil (e.g., 1,8-cineole), the surfactant (e.g., LABRASOLM, and the lactone solvent are the same as described above. Triclabendazole was found to have surprisingly good solvency in these lactone solvents (see Table VIII below) and similar lactones and combinations thereof.

TABLE VIII

Triclabendazole Solubility in Various Lactone Solvents:

| Solvent | Triclabendazole Solubility (% w/w) |
|---|---|
| γ-hexalactone. | 16.8 |
| γ-butyrolactone, | >18.0 |
| γ-dodecalactone | 11.8 |
| γ-nonalactone, | 16.7 |
| δ-decalactone, | 28.1 |
| γ-decalactone, | 15.2 |
| δ-dodecalactone | 21.5 |

What is claimed is:

1. A self-emulsifying, pour-on, veterinary anthelmintic composition comprising: a) 15 to 25% w/v of triclabendazole; and b) a water-immiscible solvent system, which comprises a lactone solvent in an amount of about 10% to about 40% w/v, wherein said lactone solvent is γ-hexalactone; an essential oil in an amount of about 29% w/v, and surfactant in an amount of about 30% to about 60% w/v, wherein the surfactant is selected from PEG-8 caprylic/capric glycerides or PEG-6 caprylic/capric glycerides.

2. The composition of claim 1, wherein the triclabendazole is present in an amount of about 20% w/v.

3. The composition of claim 1, wherein the essential oil component is 1,8-cineole.

4. The composition of claim 1, wherein the surfactant is PEG-8 caprylic/capric glycerides.

5. The composition of claim 1, which includes at least one additional anthelmintic selected from a the group consisting of macrocyclic lactone.

6. The composition of claim 5, wherein the macrocyclic lactone is moxidectin.

7. A self-emulsifying, pour-on, veterinary anthelmintic composition, comprising: about 15% to about 25% w/v of triclabendazole; and b) a water immiscible solvent system, which comprises γ-hexalactone in an amount of about 10% to about 40% w/v, 1,8-cineole in an amount of about 10% to about 35% w/v, and PEG-8 caprylic/capric glycerides in an amount of about 30% to about 60% w/v.

8. The composition of claim 7, further comprising moxidectin.

9. The composition of claim 8, wherein the moxidectin is present in an amount of about 0.01 to about 2% w/v.

10. A method of treating parasites in a homeothermic animal, said method comprising administering to said animal a self-emulsifying, pour-on, veterinary anthelmintic composition comprising: a) about 15% to about 25% w/v of triclabendazole, and b) a water-immiscible solvent system, which comprises γ-hexalactone in an amount of about 10% to about 40% w/v, about 10% to about 35% w/v of the essential oil, 1,8-cineole, and surfactant in an amount of about 30% to about 60% w/v, wherein the surfactant is PEG-8 caprylic/capric glycerides or PEG-6 caprylic/capric glycerides, and wherein said composition further comprises moxidexctin in an amount of about 0.01 to about 2% w/v.

11. The method of claim 10, wherein the triclabendazole is present in an amount of about 20% w/v, and wherein the surfactant is PEG-8 caprylic/capric glycerides.

12. A self-emulsifying, pour-on, veterinary anthelmintic composition comprising: a) 20% triclabendazole, and b) a water-immiscible solvent system, which comprises a γ-hexalactone in an amount of about 14% w/v, 1,8-cineole in an amount of about 29% w/v, and PEG-8 caprylic/caprylate as a surfactant in an amount of about 36% w/v.

* * * * *